United States Patent [19]

Amano et al.

[11] Patent Number: 5,385,830
[45] Date of Patent: Jan. 31, 1995

[54] APPARATUS FOR MEASURING FREE AND TOTAL SULFUROUS ACID AND METHOD OF MEASUREMENT

[75] Inventors: Yoshifumi Amano; Kazuo Nakamura; Hiroshi Kurosawa, all of Yamanashi; Takeshi Sato, Gifu; Hirofumi Akano; Yoshiya Kawamura, both of Aichi, all of Japan

[73] Assignee: Nakano Vinegar Co., Ltd., Aichi, Japan

[21] Appl. No.: 771,632

[22] Filed: Oct. 4, 1991

[30] Foreign Application Priority Data

Oct. 5, 1990 [JP] Japan .................. 2-266614
Nov. 29, 1990 [JP] Japan .................. 2-325586
Jul. 18, 1991 [JP] Japan .................. 3-178152

[51] Int. Cl.$^6$ .................. C12S 3/00; C12P 1/04; C12P 11/00; C12M 1/00
[52] U.S. Cl. .................. 435/29; 435/4; 436/20; 436/100; 436/119; 436/121; 436/122; 436/123; 426/535; 426/547
[58] Field of Search .................. 435/4, 29; 426/535, 426/547; 436/20, 100, 119, 121, 122, 123

[56] References Cited

PUBLICATIONS

Cooper *The Tools of Biochemistry* John Wiley & Sons pp. 12, 13 1977.
Kim et al. J Food Science vol. 51, No. 5, 1986.
Nakamura, Appl Microbiol Biotech 31: 351-354 1989.
Silverman, et al. (1959) J. Bacteriology 77:642-647.
Mulchandani, et al. (1991) J. Biotechnology 16:93-102.

*Primary Examiner*—Michael G. Wityshyn
*Assistant Examiner*—Jane Williams
*Attorney, Agent, or Firm*—Limbach & Limbach

[57] ABSTRACT

The present invention provides a method for measuring the amount of free sulfurous acid and bound sulfurous acid in a sample using a bacterium belonging to *Thiobacillus thiooxidans* or *Thiobacillus ferrooxidans* of in which the sample is treated with acid and/or alkali to give free sulfurous acid alone in the sample. Then, the total amount of free sulfurous acid in the sample is measured by an oxidation reaction of free sulfurous acid to sulfuric acid using a bacterium belonging to *Thiobacillus thiooxidans* or *Thiobacillus ferrooxidans*.

15 Claims, 13 Drawing Sheets

SAMPLE: SULFUROUS ACID (30ppm)

APPARATUS FOR MEASURING FREE AND TOTAL SULFUROUS ACID AND METHOD OF MEASUREMENT

FIELD OF THE INVENTION

The present invention relates to a method of measuring free sulfurous acid and bound sulfurous acid and to apparatuses for measuring free sulfurous acid and bound sulfurous acid. Specifically, the invention relates to a method of measuring free sulfurous acid including sulfurous acid, sodium sulfite, sodium hydrogensulfite, crystalized sodium sulfite, sodium sulfite anhydride, sodium hyposulfite, sulfurous acid anhydride and potassium metabisulfite, and bound sulfurous acid (e.g., sulfurous acid bound to aidehyde, ketone or carbohydrates).

BACKGROUND OF THE INVENTION

Free sulfurous acid and bound sulfurous acid have been widely used as food addivites for bleaching or preserving food (e.g., antioxidant) in food processing. However, it has been suggested that sulfurous acids might cause certain allergies and have harmful effects on health if the concentration of the sulfurous acids is excessive in food. In order to prevent the adverse effects of sulfurous acids on health, Food Sanitation law provides strict guidelines on the sulfurous acid content in each food item. The food industry must not only comply with the law but also take great caution regarding the sulfurous acid content in food where bound sulfurous acids are added.

Several methods have been utilized for measuring the free and bound sulfurous acid content. For example, Monier Williams method, distillation-iodometry method, distillation-colorimetry method (these methods are described in Inspection Guidelines I for Food Sanitation, 1973, Nippon Food Sanitation Association ed., p 404-408) and Rankine method (Rankine, B.C., 1962, Aust. Wine Brewing Spirit Rev 80, 14) are typically used to measure the amount of bound and free sulfurous acids in food. These methods are fairly complicated, even for skilled workers, and requires an extra step (e.g., distillation), a large amount of samples and a long period of time for analysis. Another problem with these methods is that the sulfurous acid to be measured is difficult to recover because the sulfurous acid evaporates from the system during distillation or remains as residue in the system. Alternatively, there are enzymatic methods for measuring the sulfurous acid content such as sulfuric acid oxidase recovered from the chicken liver (Beutler, H. O., 1984, Food Chem 15: 157) or instruments such as ion chromatography (Kim, H. I., Kim, Y. K., 1986, I. Food. Sci. 51 1360), gas chromatography (Hamano, H., 1978, I. Food Sanitation 19 '56), polarography (Holak, W., Specchio, I., 1989, I. Assoc. Off. Anal. Chem. 72: 476). The enzymatic method does not provide reliable results because the presence of colored substances or ascorbic acid in a sample to be tested interferes with the accurate quantitation of sulfurous acid. In addition, the enzyme itself is not stable in the sample. The methods using the instruments described above are not desirable either because the instruments are expensive or because of the drawback noted regarding the enzymatic method (e.g., interference of colored substance or ascorbic acid).

We have previously disclosed the method of measuring sulfurous acid using an enzyme recovered from a bacterium belonging to the genus Thiobacillus (Nakamura, K., Amano, Y., Nakayama, O., 1989, Appl. Microbiol. Biotechnol. 31: 351). The enzymatic method is preferable for measuring the sulfurous acid content in a sample due to the following features: specificity of the enzyme contained in the bacterium to sulfurous acid (a property which gives accurate measurement), stability of the enzyme in the bacterial cell, and ease of manipulation. The enzymatic method, however, cannot be used to measure the total sulfurous acid content (free sulfurous acid+bound sulfurous acid compounds) of the sample. This prior method is only useful for measuring the free sulfurous acid content in a sample. Therefore, a method of measuring the total sulfurous acid content in a sample is needed.

SUMMARY OF THE INVENTION

The present invention provides a method for quantitatively analyzing the free sulfurous acid or bound sulfurous acid content in a sample easily and precisely and also provides apparatuses comprising an oxygen electrode having a bacterial-cell-immobilized membrane which is stable for a long period of time and gives precise analysis of the free sulfurous acid or the bound sulfurous acid content in a sample.

DETAILED DESCRIPTION OF THE INVENTION

Figure 1:
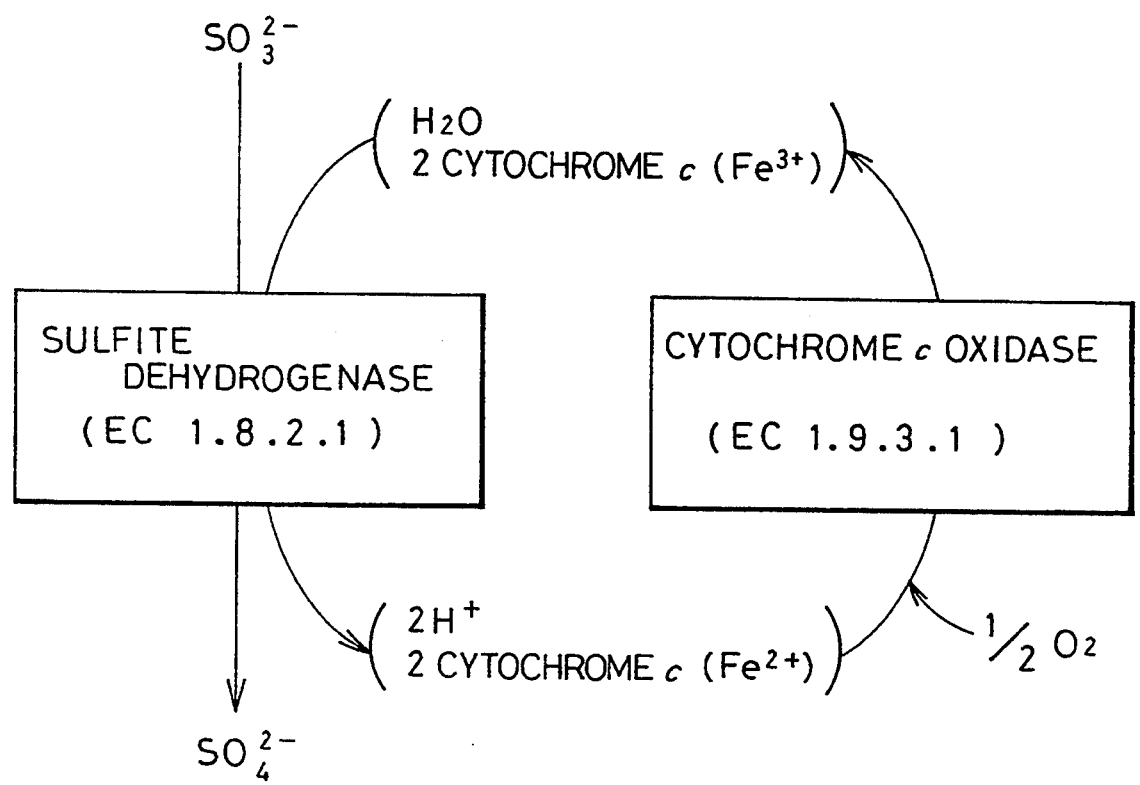
FIG. 1 shows an oxidation reaction of free sulfurous acid to sulfuric acid in the presence of bacteria.

An object of the invention is to provide a method the measuring the total sulfurous acid content in a sample accurately and easily, and to provide instruments for measuring the total sulfurous acid content in a sample.

The present invention is characterized by the following description.

(1) The invention provides a method of measuring the total sulfurous acid content of a sample comprising treating free sulfurous acid and bound sulfurous acid with acid and/or alkali to give only free sulfurous acid in the sample followed by measurement of the total amount of free sulfurous acid in the sample by oxidation of free sulfurous acid to sulfuric acid using a bacterium belonging to *Thiobacillus thiooxidans* or *Thiobacillus ferrooxidans*.

(2) The invention provides a method of measuring the bound sulfurous acid content in a sample comprising measuring the total sulfurous acid content and the free sulfurous acid content of a sample and subtracting the calculated free sulfurous acid content from the total sulfurous acid content.

In the methods described above, the free sulfurous acid content in the sample is indirectly measured by oxygen consumption, a change in the pH or the concentration of hydrogen ions present. Oxidation of free sulfurous acid to sulfuric acid occurs in the presence of bacteria, which consumes oxygen, changes the pH, and releases a hydrogen ion into the sample.

The following description will further illustrate the present invention.

Suitable microorganisms for use in the present invention include *Thiobacillus thiooxidans* strains such as IFO 13724, JCM 3866, JCM 3867, JCM 3868, ATCC 19703, ATCC 21835, 11773 (FERM BP-31 19), 20294 (FERM BP-3467), and *Thiobacillus ferrooxidans* strains such as JCM 3863, IFO 14245, IFO 14246, IFO 14262, ATCC 13598, ATCC 13661, ATCC 14119, ATCC 23270, and ATCC 33020.

In addition to these microorganisms, the present inventors have sought to identify additional bacteria which grow fast and are capable of oxidizing sulfurous acid. Inventors have successfully found bacteria belonging to the genus Thiobacillus in the soil at Matsuo mine. The bacteria has suitable properties such as being fast-growing, oxidizing sulfurous acid and being stable regarding maintaining these properties.

The properties of this bacteria is described below.

A. Morphology
(1) Shape and size of the cell: bacilliform, size: 0.4–0.8 $\mu m \times 0.9$–2.2 $\mu m$.
(2) Polymorphism: —
(3) Motility: motile, single flagellum
(4) Gram staining:
(5) Acid-fast: —

B. Culture medium
(1) The bacterium does not grow on an agar containing meat extract, a liquid medium containing meat extract, a stab culture containing meat extract and gelatin, and a litmus milk culture medium.
(2) The bacterium grows on a Thiobacillus culture medium (ATCC catalogue of bacteria and bacteriophages, 17th ed., 1989) and Thiosulphate agar No. 2 culture medium (Nei, T., et al. Method of maintaining microorganisms, University of Tokyo Press, 1977). The growth is slow and the bacterium forms very small, pale-yellow colonies.

C. Physiology
(1) Reduction of nitrate: —
(2) Denitrification: —
(3) Methyl red test: —
(4) Voges-Proskauer test: —
(5) Indole test: —
(6) Hydrogen sulfide production: —
(7) Hydrolysis of starch: —
(8) Citric acid utilization: —
(9) Inorganic nitrogen utilization: +
(10) Pigmentation: ±
(11) Urease: —
(12) Oxidase: +
(13) Catalase: —
(14) Growth condition: pH 1–6, temperature 10°–37° C.
(15) Respiration: aerobic
(16) Oxidation-fermentation test: no action on carbohydrate D. Acid or gas generation

|  | Medium | Acid | Gas |
|---|---|---|---|
| (1) | L-arabinose | — | — |
| (2) | D-xylose | — | — |
| (3) | D-glucose | — | — |
| (4) | D-mannose | — | — |
| (5) | D-fructose | — | — |
| (6) | D-galactose | — | — |
| (7) | Maltose | — | — |
| (8) | Sucrose | — | — |
| (9) | Lactose | — | — |
| (10) | Trehalose | — | — |
| (11) | D-sorbitol | — | — |
| (12) | D-mannitol | — | — |
| (13) | Inositol | — | — |
| (14) | Glycerine | — | — |
| (15) | Starch | — | — |

E. Other physiological properties
(1) Oxidation of sulfur: +
(2) Oxidation of iron ion: —
(3) Oxidation of thiosulfuric acid: +
(4) Nutrient: lithotrophic
(5) Generation of sulfate: +

F. Chemical properties
(1) GC content in DNA: 51 mol %
(2) Ubiquinone: ubiquinine Q-8
(3) Fatty acid in cells: 3-hydroxytetradecanoic acid The bacterium was classified by Bergey's Manual of Systematic Bacteriology Volume 3, 1989 according to the properties described above. The bacterium was found to be a bacterium belonging to *Thiobacillus thiooxidans* and was designated as *Thiobacillus thiooxidans* 11773. *Thiobacillus thiooxidans* 11773 was deposited with Fermentation Research Institute, Agency of Industrial Science and Technology and was assigned the accession number FERM BP-3119.

The present inventors have identified another suitable bacterium belonging to the genus Thiobacillus in the soil at Noji hot spring. This bacterium is also fast-growing, capable of oxidizing sulfurous acid and stable with regard to maintaining those properties.

Properties of the bacterium are described below.

Morphology
(1) Shape and size of the cell: bacilliform, size: 0.5–0.7 $\mu m \times 1.0$–2.2 $\mu m$.
(2) Polymorphism: —
(3) Motility: motile, single flagellum
(4) Gram staining: —
(5) Acid-fast: —

B. Culture medium
(1) The bacterium does not grow on an agar containing meat extract, a liquid medium containing meat extract, a stab culture containing meat extract and gelatin, and a litmus milk culture medium.

(2) The bacterium grows on a Thiobacillus culture medium (ATCC catalogue of bacteria and bacteriophages, 17th ed., 1989) and Thiosulphate agar No. 2 culture medium (Nei, T., et al. Method of maintaining microorganisms, University of Tokyo Press, 1977). The growth is slow and the bacterium forms very small, pale-yellow colonies.

C. Physiology
(1) Reduction of nitrate: −
(2) Denitrification: −
(3) Methyl red test: −
(4) Voges-Proskauer test: −
(5) Indole test: −
(6) Hydrogen sulfide production: −
(7) Hydrolysis of starch: −
(8) Citric acid utilization: −
(9) Inorganic nitrogen utilization: +
(10) Pigmentation: ±
(11) Urease: −
(12) Oxidase: +
(13) Catalase: −
(14) Growth condition: pH 1.5–5.5, temperature 10°–37° C.
(15) Respiration: aerobic
(16) Oxidation-fermentation test: no action on carbohydrate D. Acid or gas generation

|  | Medium | Acid | Gas |
| --- | --- | --- | --- |
| (1) | L-arabinose | − | − |
| (2) | D-xylose | − | − |
| (3) | D-glucose | − | − |
| (4) | D-mannose | − | − |
| (5) | D-fructose | − | − |
| (6) | D-galactose | − | − |
| (7) | Maltose | − | − |
| (8) | Sucrose | − | − |
| (9) | Lactose | − | − |
| (10) | Trehalose | − | − |
| (11) | D-sorbitol | − | − |
| (12) | D-mannitol | − | − |
| (13) | Inositol | − | − |
| (14) | Glycerine | − | − |
| (15) | Starch | − | − |

E. Other physiological properties
(1) Oxidation of sulfur: +
(2) Oxidation of iron ion: −
(3) Oxidation of thiosulfuric acid: +
(4) Nutrient: lithotrophic
(5) Generation of sulfate: +

F. Chemical properties
(1) GC content in DNA: 51 mol %
(2) Ubiquinone: ubiquinone Q-8
(3) Fatty acid in cells: 3-hydroxytetradecanoic acid The bacterium was classified by Bergey's Manual of Systematic Bacteriology Volume 3, 1989 according to the properties described above. The bacterium was found to be a bacterium belonging to *Thiobacillus thiooxidans* and was designated as *Thiobacillus thiooxidans* 20294. *Thiobacillus thiooxidans* 20294 was deposited with Fermentation Research Institute, Agency of Industrial Science and Technology and was assigned the accession number FERM BP-3467.

The bacteria belonging to *Thiobacillus thiooxidans* described above can be grown on solid media such as silverman 9K containing sulfur (Silverman., M. P. et al., I. Bacteriol., 77: 642, 1959), thiobacillus medium (ATCC catalogue of bacteria and bacteriophages 17th ed., 1989), and thiosulphate agar No. 2 medium (Nei, T., et al. Method of maintaining microorganisms, University of Tokyo Press, 1977), or any of the above media with modification. Suitable culture temperature may be 10°–37° C., preferably 25°–33° C. Suitable medium pH may be pH 1–6, preferably pH 3–5. Suitable incubation time may be 2–10 days, preferably 3–10 days. The growth culture may be liquid or solid under good aeration.

Once grown, the bacteria of the invention can be used for measuring sulfurous acid. The measurement can be carried out using whole cells, disrupted cells or crude enzyme extracted from cells. Whole cells are prepared by filtration of culture to remove sulfur residue. Fractions and crude enzyme are prepared from disrupted whole cells. If desired, bacterial cells can be immobilized between acetylcellulose membrane filters (pore size: less than 0.45 $\mu$m). Immobilization keeps the bacterial cells in place, which maintains the stable oxidization of sulfurous acid. Amano has described, in a lecture summary of wine-making technology, vol 2, 1988, that free sulfurous acid is oxidized to sulfuric acid by an enzyme contained in *Thiobacillus thiooxidans* named sulfite dehydrogenase. Sulfite dehydrogenase oxidizes free sulfurous acid to sulfuric acid in the presence of cytochrome c ($Fe^{3+}$) and $H_2O$. The resulting cytochrome c ($Fe^{2+}$) and are oxidized by cytochrome c oxidase to cytochrome c ($Fe^{3+}$) and $H_2O$ in the presence of oxygen. The reaction series described above is shown in FIG. 1. *Thiobacillus ferrooxidans* also possesses an enzyme that oxidizes free sulfurous acid in the presence of an iron ion (Hakkokogaku 67 (3): p173, 1989).

Although methods for measuring the free sulfurous acid content in a sample are known, no method for measuring the total sulfurous acid content or the bound sulfurous acid content of a sample has been taught. As a result, the bound sulfurous acid content of samples have not been calculated.

We have found that the treatment described below separates free sulfurous acid from bound sulfurous acid. Samples containing bound sulfurous acid are treated with acid under the conditions in which the pH is pH 1–3, preferably pH 1.5–3, temperature is 70°–110° C., preferably 75°–105° C. and incubation time is 2–25 minutes, preferably 5–20 minutes. Similarly, samples containing bound sulfurous acid are treated with alkali under the conditions in which pH is pH 10–14, preferably pH 11–13, temperature is 15°–70° C., preferably 20°–50° C. and incubation time is 2–20 minutes, preferably 5–15 minutes. The resulting samples contain free sulfurous acid alone. After acid or alkaline treatment, the total amount of free sulfurous acid is determined as described above. Thus, the free and total sulfurous acid content in the sample can be calculated depending on whether bound sulfurous acid is first converted to free sulfurous acid. The bound sulfurous acid content of a sample can be calcualted by subtracting the free sulfurous acid content from the total sulfurous acid content of a sample. The sulfurous acid in the samples are converted to all free sulfurous acid by the addition of acid or alkali in situ. The total amount of the resulting free sulfurous acid in the samples is determined by an oxygen electrode having a bacterial-cell-immobilized membrane (hereafter referred to as oxygen-microbe electrode). By not having to remove the sulfurous acid from the sample, by, for example, distillation, loss of sulfurous acid by evaporation is prevented.

Free sulfurous acid is oxidized to sulfuric acid in the presence of the bacteria described above. In the process of oxidizing sulfurous acid to sulfuric acid, the oxygen consumed by the bacteria can be closely correlated to release of a hydrogen ion. This suggests that the amount of oxygen consumed and the number of hydrogen ions released can be determined by monitoring changes in electric current or potential using an oxygen electrode or a pH meter, which in turn indicates an free sulfurous acid content in the sample.

Figure 2:
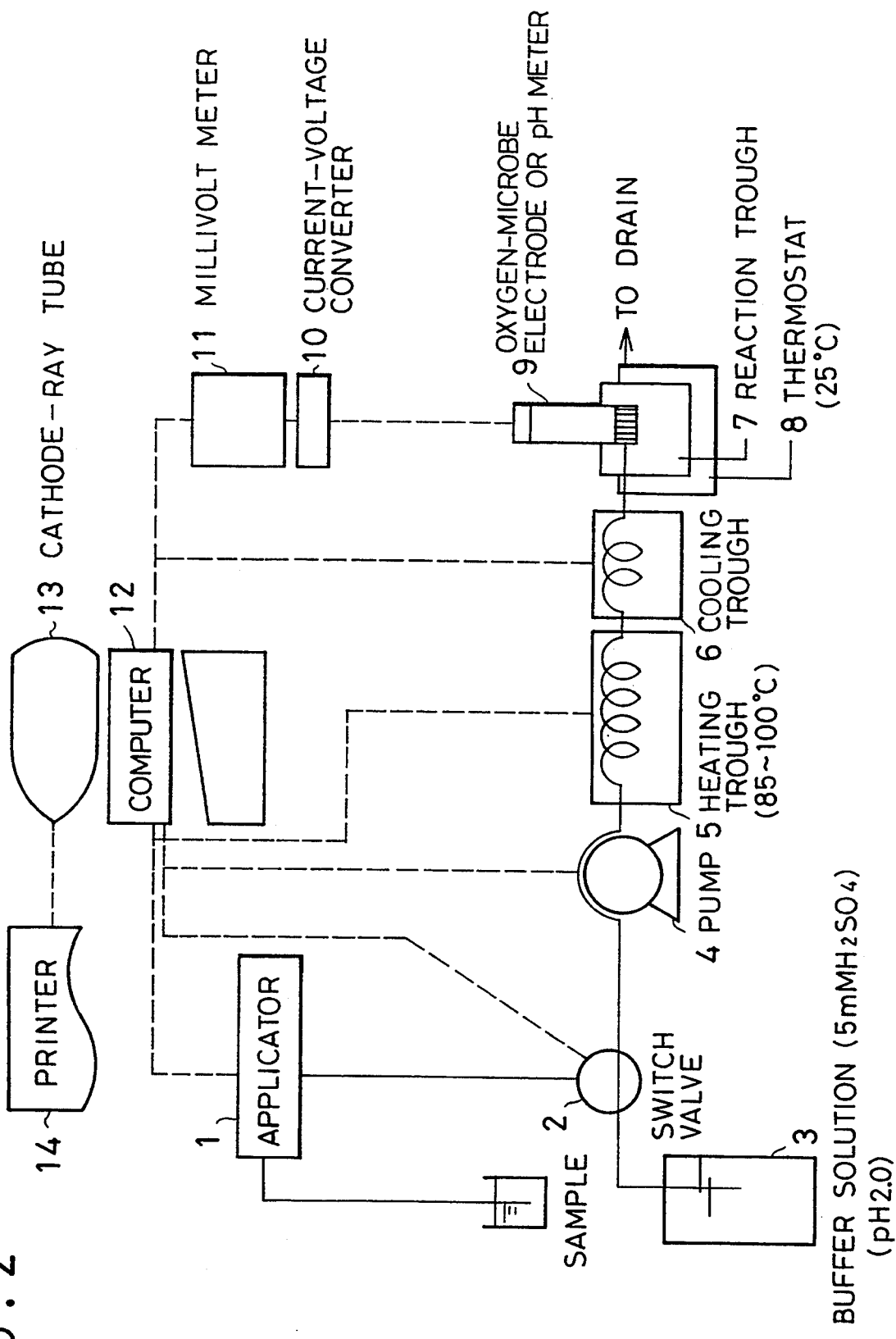
FIG. 2 shows an acid treatment type apparatus of the invention.

FIG. 2 shows a circuit diagram of an apparatus of the invention where acid is used to treat samples. The apparatus for measuring the amount of sulfurous acid present comprises an applicator 1, a switch valve 2 to select either a sample or a buffer, a pump 4 to draw the sample and the buffer toward a heating trough 5 where the sample and the buffer are mixed and heated, a cooling trough 6 to cool the mixture heated in the heating trough, a reaction trough 7 equipped with either an oxygen electrode having a bacterial-cell-immobilized membrane or a biosensor equipped pH meter, a thermostat 7 to maintain a constant temperature of the reaction trough, a current-voltage converter 10, a millivolt meter 11, a computer 12, a cathode-ray tube 13 and a printer 14.

A given amount of a sample is drawn from the applicator 1 by the pump 4 and is sent to the heating trough 5 by the pump 4. When the switch valve 2 is in a buffer position, buffer solution 3 is drawn to the heating trough 5 where the sample and the buffer solution 3 are mixed and heated. The mixture is then sent to the cooling through 6, cooled, sent to the reaction trough 7 whose temperature is kept constant by the thermostat 8. The reaction trough 7 is equipped with either an oxygen electrode having a bacterial-cell-immobilized membrane or a biosensor equipped pH meter which measures change in electric potential. The measured signal is fed into the computer 12 via the current-voltage converter 10 and the millivolt meter 11 and is processed by the computer 12. After processing, results are shown on a cathode-ray tube screen 13 or printed out by a printer 14. This series of manipulations are programmed on the computer and can be automatically controlled by the computer.

Figure 3:
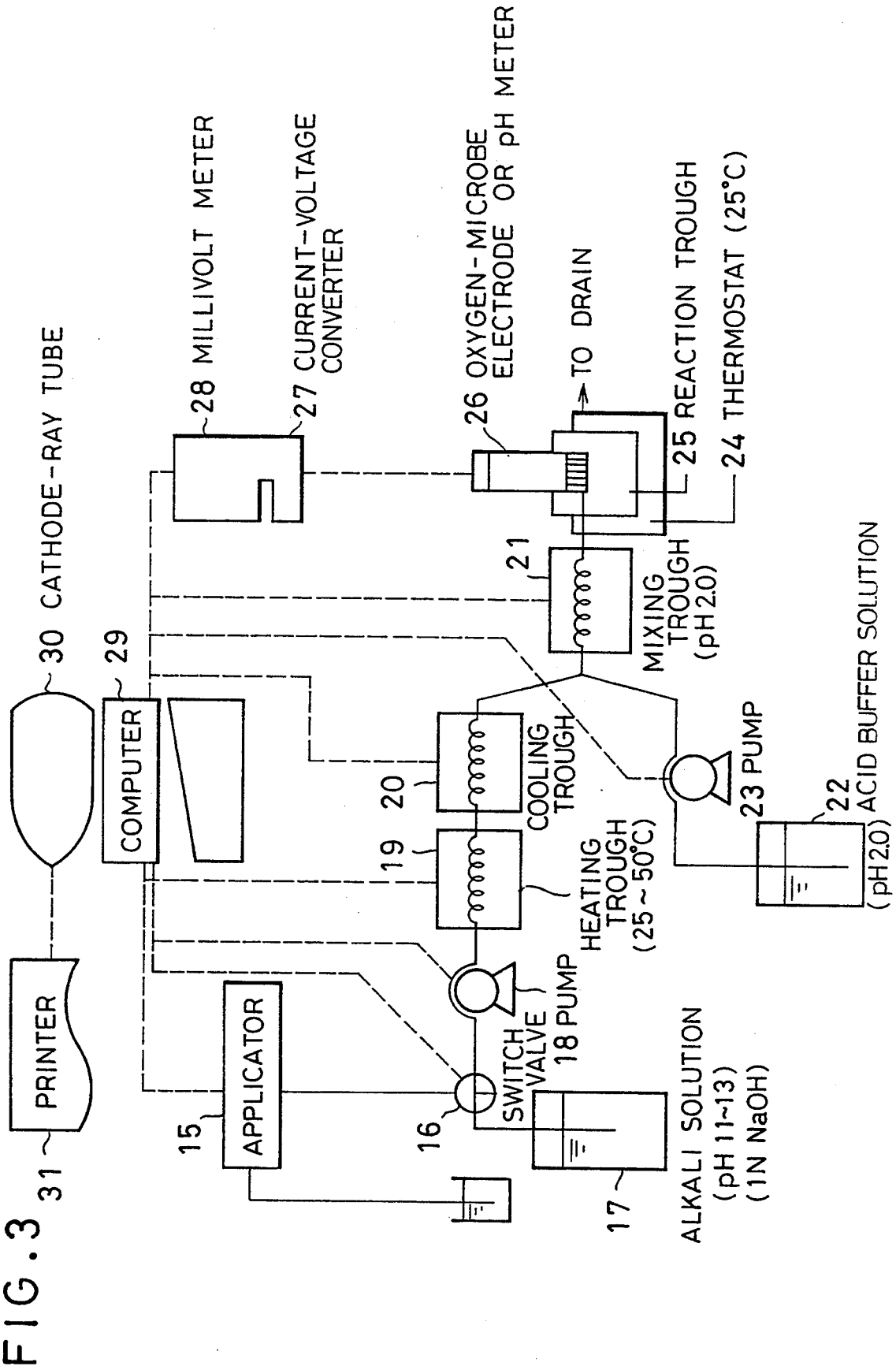
FIG. 3 shows an alkali treatment type apparatus of the invention.

FIG. 3 shows a circuit diagram of an apparatus of the invention where alkali is used to treat samples. The apparatus for measuring the amount of sulfurous acid present comprises an applicator 15, a switch valve 16 to select either a sample or a buffer, a pump 18 to draw the sample and the buffer solution toward a heating trough 19 where the sample are treated with alkali, a cooling trough 20 to cool the alkali-treated sample, a pump 23 to send acid to a mixing trough 21 where the sample and acid are mixed, a reaction trough 25 equipped with either an oxygen electrode having a bacterial-cell-immobilized membrane or a biosensor equipped pH meter, a thermostat 24 to maintain a constant temperature of the reaction trough, a current-voltage converter 27, a millivolt meter 28, a computer 29, a cathode-ray tube 30 and a printer 31.

A given amount of a sample is drawn from the applicator 15 by the pump 18 and is sent to the heating trough 19 by the same pump 18. When the switch valve 16 is in an alkali solution position, the alkali solution is drawn to the heating trough 19 where the sample is treated with alkali. The alkali-treated sample is then sent to the cooling trough 20, cooled, sent to the mixing trough 21 where the alkali-treated sample is mixed with acid 22 which is drawn by the pump 23. The mixture is then sent to the reaction trough 25 whose temperature is kept constant by the thermostat 24. The reaction trough 25 is equipped with either an oxygen electrode having a bacterial-cell-immobilized membrane or a biosensor equipped pH meter which measures change in electric potential. The measured signal is fed into the computer 29 via the current-voltage converter 27 and the millivolt meter 28 and is processed by the computer 29. After processing, results are shown on a cathode-ray tube screen 30 or printed out by a printer 31. This series of manipulations are programmed on the computer and can be automatically controlled by the computer.

The invention will be further described by the following Examples, which are not intended to limit the scope of the invention.

EXAMPLE 1

(1) Culture Method of *Thiobacillus thiooxidans* 11773 (FERM BP-3119)

*Thiobacillus thiooxidans* 11773 (FERM BP-31 19) was inoculated into 50 ml of a medium (described below) in a 200 ml Erlenmeyer flask.

| Medium Composition | |
|---|---|
| Powdered sulfur | 1.0% |
| $K_2HPO_4$ | 0.05% |
| $Ca(NO_3)_2 4H_2O$ | 0.001% |
| $(NH_4)_2SO$ | 40.3% |
| KCl | 0.01% |
| $MgSO_4 7H_2O$ | 0.05% |

**The chemical agent was dissolved in distilled water and the pH was adjusted to pH 6.5

The culture was incubated with shaking at 30° C. for 4 days. After incubation, 2 ml of the 4-day culture was added to 100 ml of the same medium described above in a 300 ml Erlenmeyer flask. The culture was incubated with shaking at 30° C. for 10 days. After incubation, the culture was filtrated using No. 5C filter (Toyo Roshi) to remove sulfur. The resulting filtrate was found to contain 0.2 g/l (dry weight) of bacterial cells.

(2) Culture of Bacteria belonging to *Thiobacillus thiooxidans* and *Thiobacillus ferrooxidans* and Comparison of Oxygen Uptake Rate.

Bacteria belonging to *Thiobacillus thiooxidans* or *Thiobacillus ferrooxidans* (see Table 1) were inoculated into 100 ml of the medium described in (1) in a 300 ml Erlenmeyer flask to a final concentration of 10 mg/l of bacterial cells (dry weight). The culture was incubated with shaking at 30° C. for 4 days.

After incubation, the culture was filtrated using No. 5C filter (Toyo Roshi) to remove sulfur. The bacterial cells thus obtained were weighed to measure their growth rate and tested for their oxygen uptake rate as an indicator of their ability to oxidize sulfurous acid.

The oxygen uptake rate was measured by an oxygen uptake meter(Rank Broth Co) using sodium sulfite as the oxidation substrate. Table 1 shows the results.

TABLE 1

| Bacterium | Dry weight (g/l) | Oxygen uptake rate (mgO$_2$/min/g dry weight) |
|---|---|---|
| *Thiobacillus thiooxidans* | | |
| IFO 13724 | 0.05 | 3 |
| JCM 3866 | 0.06 | 4 |
| JCM 3867 | 0.05 | 4 |
| JCM 3868 | 0.06 | 3 |
| 11773 | 0.10 | 7 |

TABLE 1-continued

| Bacterium | Dry weight (g/l) | Oxygen uptake rate (mgO₂/min/g dry weight) |
|---|---|---|
| 20294 | 0.15 | 15 |
| *Thiobacillus ferrooxidans* | | |
| JCM 3863 | 0.05 | 5 |
| IFO 14245 | 0.08 | 5 |
| IFO 14246 | 0.02 | 6 |
| IFO 14262 | 0.02 | 4 |
| ATCC 13661 | 0.02 | 3 |
| ATCC 13598 | 0.04 | 5 |
| ATCC 14119 | 0.07 | 4 |
| ATCC 23270 | 0.06 | 4 |
| ATCC 33020 | 0.02 | 5 |

(3) Immobilizing Bacterial Cells on Membrane

The filtrate described in (2) was centrifuged at 11,000 rpm for 15 minutes. The resulting cell pellet was suspended in a small amount of ice cold distilled water and then the suspension was centrifuged for washing the cell. The washing procedure was repeated twice. After washing, the cells were resuspended in 0.1M sodium citrate-NaOH buffer/pH 6.0 to a final concentration of 5 g/l (dry weight). 50 μl of the suspension was placed in the space of an acetylcellulose membrane sandwich.

Figure 4:
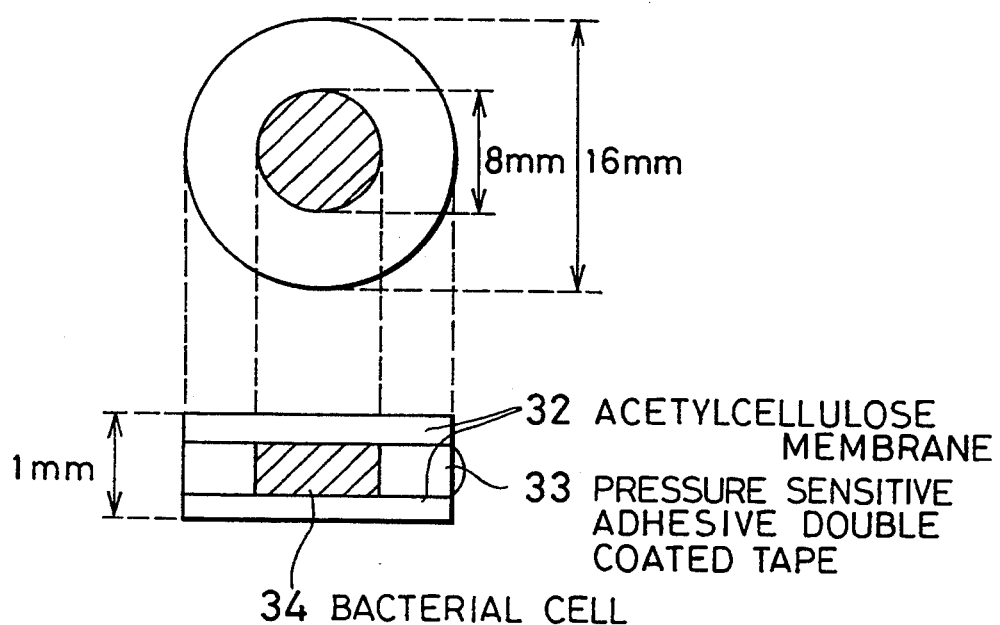
FIG. 4 shows an acetylcellulose membrane specifically made to immobilize bacterial cells.

The acetylcellulose membrane sandwich was made as follows: a pressure sensitive adhesive double coated tape 33 (16 mm in diameter) with a 8 mm-hole in center was sandwiched between acetylcellulose membrane filters 32 [16 mm in diameter, pore size: 0.45 μm (Millipore)] (FIG. 4). Suction was applied to one side of the membrane to immobilize bacterial cells.

Another membrane filter for immobilizing bacterial cells was made as follows: membrane filters were overlayed onto the immobilized bacterial cells. The membrane filter containing the immobilized bacterial cells was stable at 4° C. for 3 months.

(4) Measurement of Samples Using Oxygen-Microbe Electrode

Figure 5:
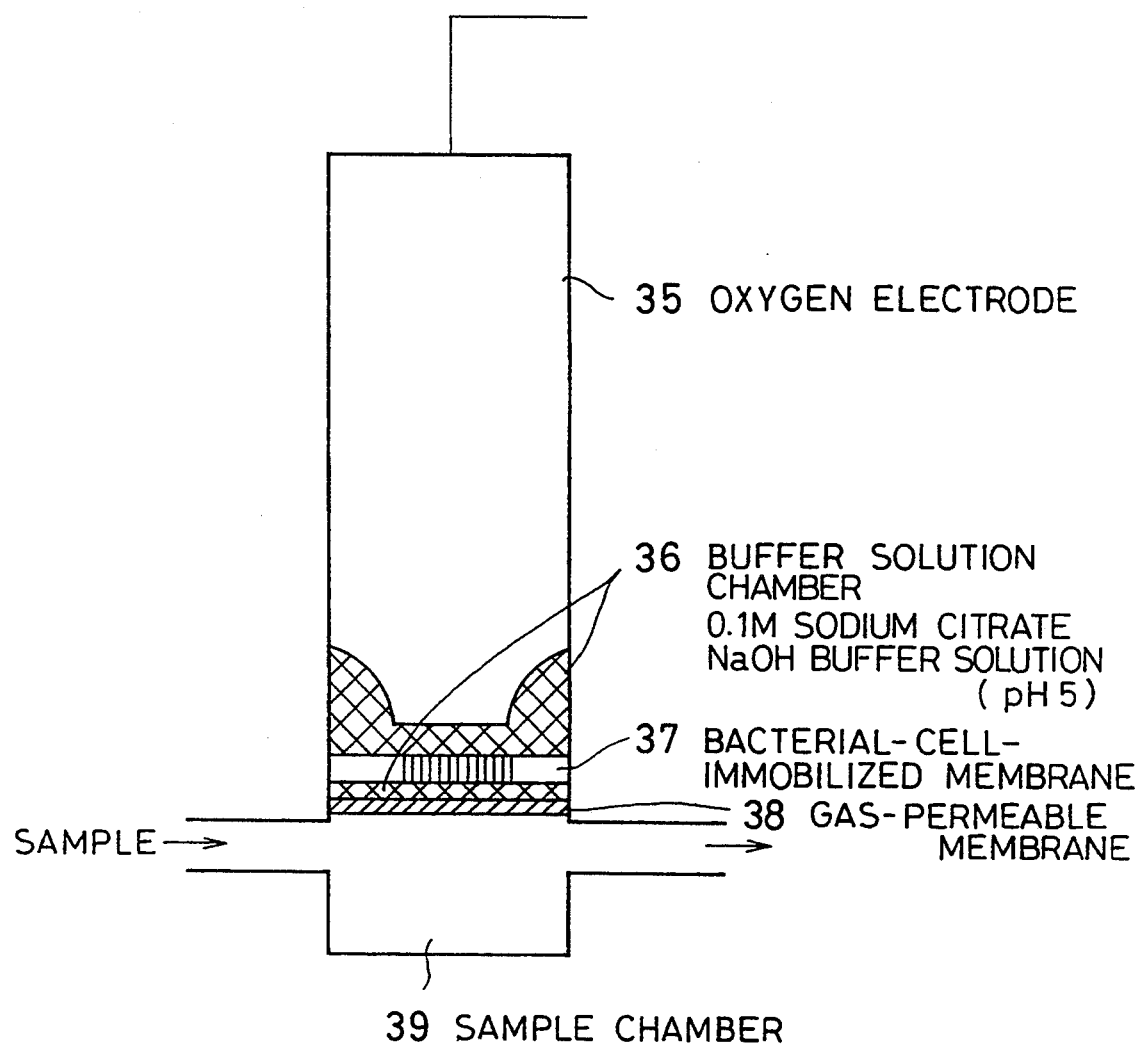
FIG. 5 shows an oxygen electrode having a bacterial-cell-immobilized membrane.
Figure 6:
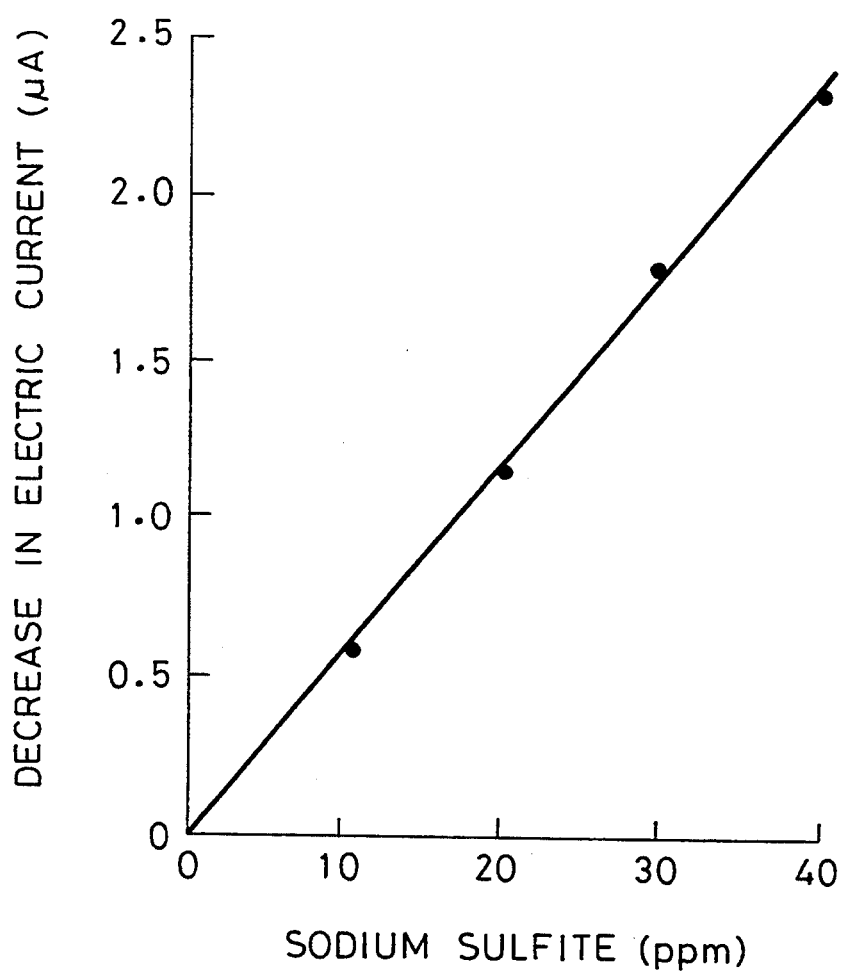
FIG. 6 is a linear curve illustrating the relationship between the concentration of sodium sulfite and the decrease in electric current.

A bacterial-cell-immobilized membrane 37 described in (3) was plugged into the top of an oxygen electrode 35 (Denkikagaku Keiki CO.,) (See FIG. 5). A buffer solution chamber 36 was first filled with 0.1M sodium citrate-NaOH buffer solution/pH 5.0. The top of the oxygen electrode 35 was then capped with a membrane 38 permeable to gas (phloropore filter, Sumitomo Electric Co.). The oxygen-microbe electrode was installed in the reaction trough of an acid treatment type apparatus of the invention shown in FIG. 2. An increased concentration of sodium sulfite (10–40 ppm) was prepared as a standard. The oxygen-microbe electrode was then tested for a decrease in an electric current by the increased concentration of sodium sulfite standard. The concentration of sodium sulfite was found to be inversely proportional to the electric current (FIG. 6).

(5) Conditions of Treating Sulfurous Acid Containing Compounds for Quantitative Analysis Suitable conditions for treating sulfurous acid containing compounds were determined using a compound of sulfurous acid combined with glutaraldehyde as a standard; acid treatment of the compound is shown in Table 2, and alkaline treatment of the compound is shown in Table 3.

TABLE 2

Acid treatment
Sample: glutaraldehyde-sulfurous acid compound (30 mg/l)

| pH | 0.5 | 1 | 1.5 | 2.0 | 2.5 | 3.0 | 3.5 | 4.0 |
|---|---|---|---|---|---|---|---|---|
| Concentration in test (mg/l) | 32 | 31 | 30 | 30 | 30 | 30 | 28 | 25 |
| Yield (%) | 107 | 103 | 100 | 100 | 100 | 100 | 93 | 83 |

(90° C. 10-minute treatment)

| Temperature (°C.) | 60 | 65 | 70 | 75 | 80 | 90 | 10 | 105 | 110 | 115 |
|---|---|---|---|---|---|---|---|---|---|---|
| Concentration in test (mg/l) | 25 | 28 | 29 | 30 | 30 | 30 | 31 | 31 | 35 | 34 |
| Yield % | 83 | 93 | 97 | 100 | 100 | 100 | 100 | 103 | 117 | 113 |

(pH 2.0, 10-minute treatment)

| Time (minute) | 1 | 2 | 3 | 5 | 10 | 15 | 20 | 25 | 30 |
|---|---|---|---|---|---|---|---|---|---|
| Concentration in test (mg/l) | 28 | 29 | 29 | 30 | 30 | 31 | 30 | 32 | 33 |
| Yield % | 93 | 97 | 97 | 100 | 100 | 104 | 100 | 107 | 110 |

(pH 2.0, 90° C. treatment)

TABLE 3

Alkaline treatment
Sample: glutaraldehyde sulfurous acid compound (30 mg/l)

| pH | 8 | 9 | 10 | 11 | 12 | 13 | 14 |
|---|---|---|---|---|---|---|---|
| Concentration in test (mg/l) | 27 | 28 | 29 | 30 | 30 | 31 | 29 |
| Yield % | 90 | 93 | 96 | 100 | 100 | 104 | 96 |

(30° C., 10-minute treatment)

| Temperature (°C.) | 10 | 15 | 20 | 30 | 40 | 50 | 60 | 70 | 80 | 90 |
|---|---|---|---|---|---|---|---|---|---|---|
| Concentration in test (mg/l) | 27 | 29 | 29 | 30 | 30 | 31 | 30 | 31 | 33 | 33 |
| Yield % | 90 | 97 | 97 | 100 | 100 | 04 | 100 | 104 | 110 | 110 |

(pH 12, 10-minute treatment)

| Time (minute) | 1 | 2 | 3 | 5 | 10 | 15 | 20 | 25 | 30 |
|---|---|---|---|---|---|---|---|---|---|
| Concentration in test (mg/l) | 28 | 29 | 29 | 30 | 30 | 30 | 31 | 32 | 31 |
| Yield % | 93 | 97 | 97 | 100 | 100 | 100 | 104 | 107 | 114 |

(pH 12, 30° C. treatment)

Suitable acid treatment conditions were found as follows:
  pH: pH 1–3, preferably pH 1.5–3,
  temperature: 70°–110° C., preferably 75°–105° C.,
  time: 2–25 minutes, preferably 5–10 minutes.
Suitable alkaline treatment conditions were found as follows:

pH: pH 10-14, preferably pH 1114 13,
temperature: 15°-70° C., preferably 20°-50° C.,
time: 2-20 minutes, preferably 5-15 minutes.

(6) Quantitative Analysis of Sulfurous Acid Containing Compounds After Acid or Alkaline Treatment An oxygen-microbe electrode was installed in the reaction trough (FIGS. 2 and 3). A glutaraldehyde-sulfurous acid compound was tested and the results are shown in Tables 4 and 5.

Additionally, the same sample was tested according to Rankine's method and the results are shown in Table 6.

TABLE 4

Quantitative analysis of sulfurous acid containing compounds after acid treatment

| Sample Concentration (mg/l) | Concentration in test (mg/l) | Yield (%) |
|---|---|---|
| 5 | 4.9 | 98 |
| 10 | 10.0 | 100 |

Sample: glutaraldehyde-sulfurous acid compound
Treatment condition: pH 2.0, 70° C., 5 minutes

TABLE 5

Quantitative analysis of sulfurous acid containing compounds after alkaline treatment

| Sample Concentration (mg/l) | Concentration in test (mg/l) | Yield (%) |
|---|---|---|
| 110 | 109 | 99 |
| 50 | 51 | 102 |

Sample: glutaraldehyde-sulfurous acid compound
Treatment condition: pH 12, 25° C., 5 minutes

TABLE 6

Quantitative analysis of sulfurous acid containing compounds containing compounds according to Rankine's method

| Sample Concentration (mg/l) | Concentration in test (mg/l) | Yield (%) |
|---|---|---|
| 5 | 3 | 60 |
| 10 | 8 | 80 |
| 50 | 48 | 96 |
| 100 | 95 | 95 |

Sample: glutaraldehyde-sulfurous acid compound
Method of measurement: Test methods for Food Sanitation, annotated ed., 1990, Japanese Pharmacology Society ed., Kanehara Press, P.475

The content of bound sulfurous acid was quantitatively analyzed precisely and quickly according to the apparatus of the invention.

(7) Analysis of Total Sulfurous Acid Content in Wine and Comparison Study

The total and free sulfurous acid content in wine were analyzed by the alkaline treatment type apparatus of the invention illustrated in FIG. 3 and by the Rankine technique. The results are shown in Table 7 and 8.

TABLE 7

Total sulfurous acid content in wine (1)

| | Analytical method | |
|---|---|---|
| | Alkaline treatment | Rankine's method |
| Total sulfurous acid (mg/l) | 209 | 219 |

Sample: white wine
Treatment: alkali (pH 12, 30° C., 5 minutes)
The figures are an average of six measurements.

TABLE 8

Free sulfurous acid content in wine (2)

| | Analytical method | |
|---|---|---|
| | Alkaline treatment | Rankine's method |
| Total sulfurous acid (mg/l) | 6.9 | 7.0 |
| Total sulfurous (mg/l) | 186 | 181 |

Sample: red wine
Treatment: free sulfurous-not treated sulfurous acid containing compounds - alkaline treatment (pH 12, 30° C., 5 minutes)
The numbers represent an average of 6 measurements.

(8) Oxygen-Microbe Electrode

Figure 7:
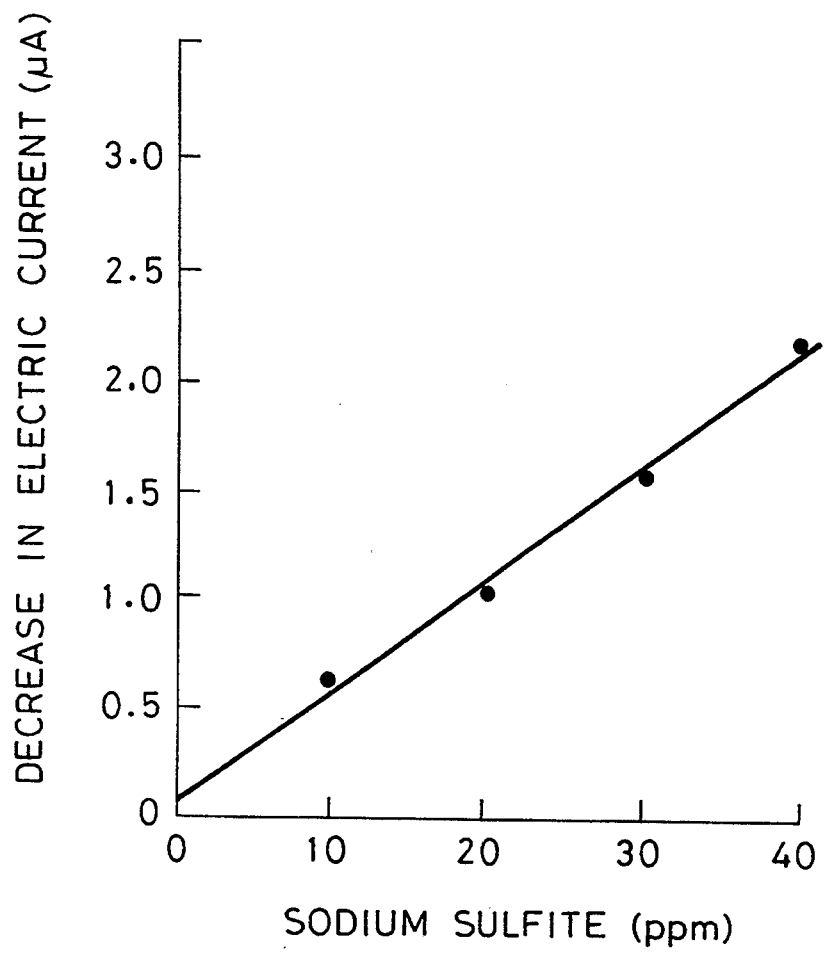
FIG. 7 is a linear curve illustrating the relationship between the concentration of sodium sulfite and the decrease in electric current.

*Thiobacillus ferrooxidans* IFO 14246 was cultured as described in (1) and 0.08 g/l (dry weight) of bacterial cells was harvested. The bacterial cells were immobilized on the membrane as described in (3) and the bacterial-cell-immobilized membrane was plugged in an oxygen electrode 35 (Denkikagaku Keiki) illustrated in FIG. 5. The buffer chamber 36 of the oxygen-microbe electrode was filled with 0.1M sodium citrate-NaOH buffer solution/pH 5.0 and the oxygen-microbe electrode was capped with a membrane 38 permeable to gas (Fluro filter, Sumitomo Electric Co.). The oxygen-microbe electrode was installed in an acid treatment type apparatus illustrated in FIG. 2. The oxygen-microbe electrode was then tested for a decrease in the electric current by the increased concentration of sodium sulfite standard (10-40 ppm). The concentration of sodium sulfite was found to be inversely proportional to the electric current (FIG. 7).

The advantages of *Thiobacillus ferrooxidans* IFO 14246 were that it grew fast and a small scale of the culture provided an adequate amount of bacterial cells.

EXAMPLE 2

(a) Quantitative Analysis of Sulfurous Acid by Suspended Process Using pH Meter

Figure 8:
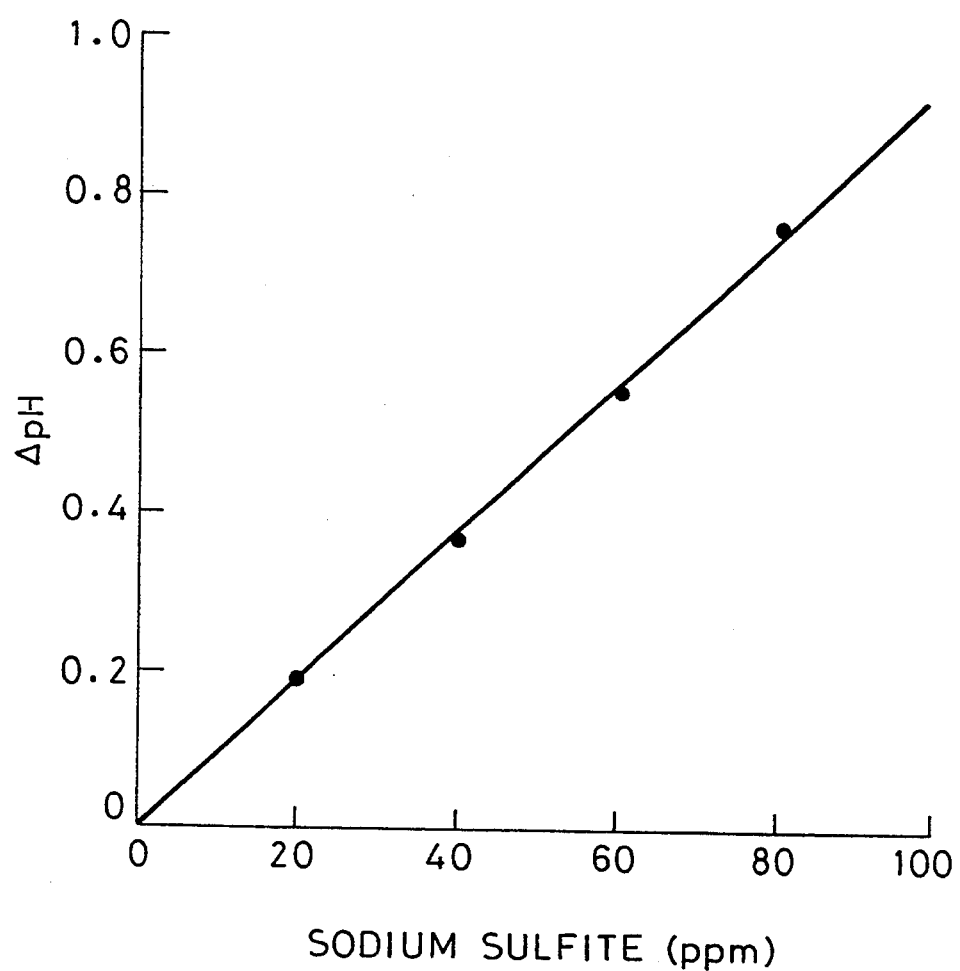
FIG. 8 is a linear curve illustrating the relationship between the change in pH and the concentration of sodium sulfite.

A glass electrode of a pH meter was installed in a reaction trough (FIGS. 2 and 3). Bacterial cells described in (1) were suspended in a 1 mM sodium citrate-NaOH buffer solution/pH 6.0 to a final concentration of 1 g/l. The suspension was then placed in the reaction trough. Sodium sulfite was injected into the reaction trough to a final concentration of 0-100 ppm. Different concentrations of sodium sulfite were tested at 30° C. for 20 minutes. The results suggested that the concentration of sodium sulfite is closely correlated to the change in (FIG. 8).

(b) Quantitative Analysis of Sulfurous Acid in Reaction Trough Using Biosensor Equipped pH Meter A bacterial-cell-immobilized membrane was plugged into the glass electrode of a pH meter (Flat glass valve 39533, Beckman) (hereafter referred to as biosensor equipped pH meter) and the biosensor equipped pH meter was installed in the trough (see FIG. 2).

1) Theoretical background for measuring sulfurous acid with pH change

Figure 9:
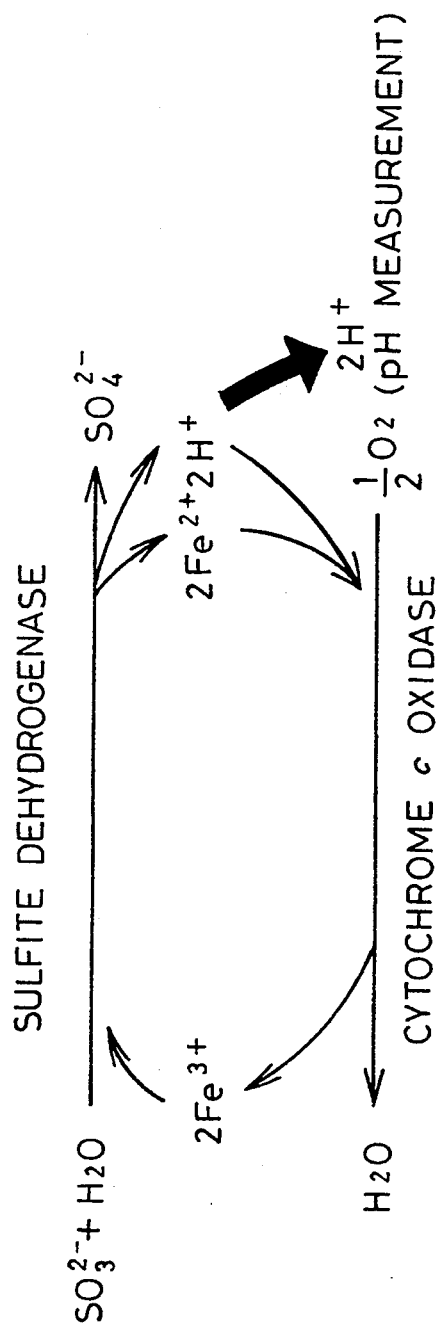
FIG. 9 illustrates hydrogen ion generation in the oxidation reaction of sulfurous acid in the presence of *Thiobacillus thiooxidans.*

Sulfurous acid is oxidized to sulfuric acid in the presence of *Thiobacillus thiooxidans*, which is accompanied by the generation of a hydrogen ion. The number of hydrogen ions generated is proportional to the oxidation of sulfurous acid (see FIG. 9). The sulfurous acid content in the sample is thus calculated by measuring the pH change ($\Delta pH$).

2) Suitable buffer solution and its concentration, and time for measurement

Various concentrations of buffer solutions have been tried. Inventors have found that 2.5 mM sodium phosphate buffer solution containing 0.1M NaCl (NaCl reduces a deviation of measured values and serves to increase reproducibility) was suitable for measurement since a significant change in pH was observed and the resulting data was reproducible. Higher concentrations of the buffer solution decreased the observed change in the pH and lower concentrations (e.g., 1 mM) of the buffer solution did not give reproducible data. It was observed that the change in the pH increased during the first 10 minutes but then decreased. Since a significant pH change is observed during the first 10 minutes and since that pH change is proportional to the amount of sulfurous acid oxidized, it is recommended that samples be measured over the first 10 minutes.

3) Starting pH

Figure 10:
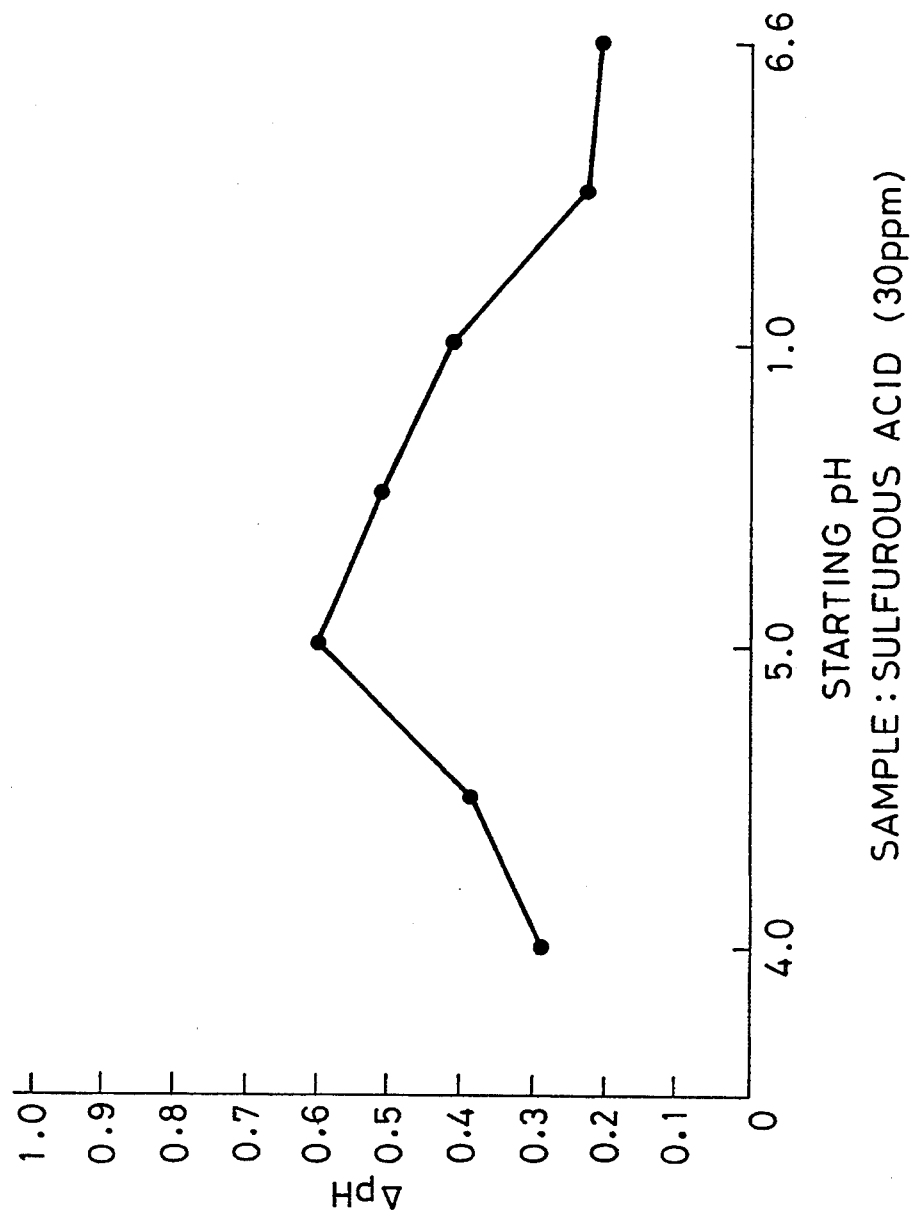
FIG. 10 is a graph representing the relationship between the pH change and the starting pH of a buffer solution.

The suitable initial pH range for the buffer solution was found to be 4.5–6.0. Initial buffer pH's lower than pH 4.5 and higher than pH 6.0 reduced the resulting change in pH and were thus not suitable for measurement (see FIG. 10). FIG. 10 shows the relationship between the change in the pH and the starting pH of the buffer solution under conditions; 10 minutes for measurement, starting pH 5.0, 30° C. and 2.5 mM sodium phosphate buffer solution containing 0.1M NaCl.

4) Temperature

Figure 11:
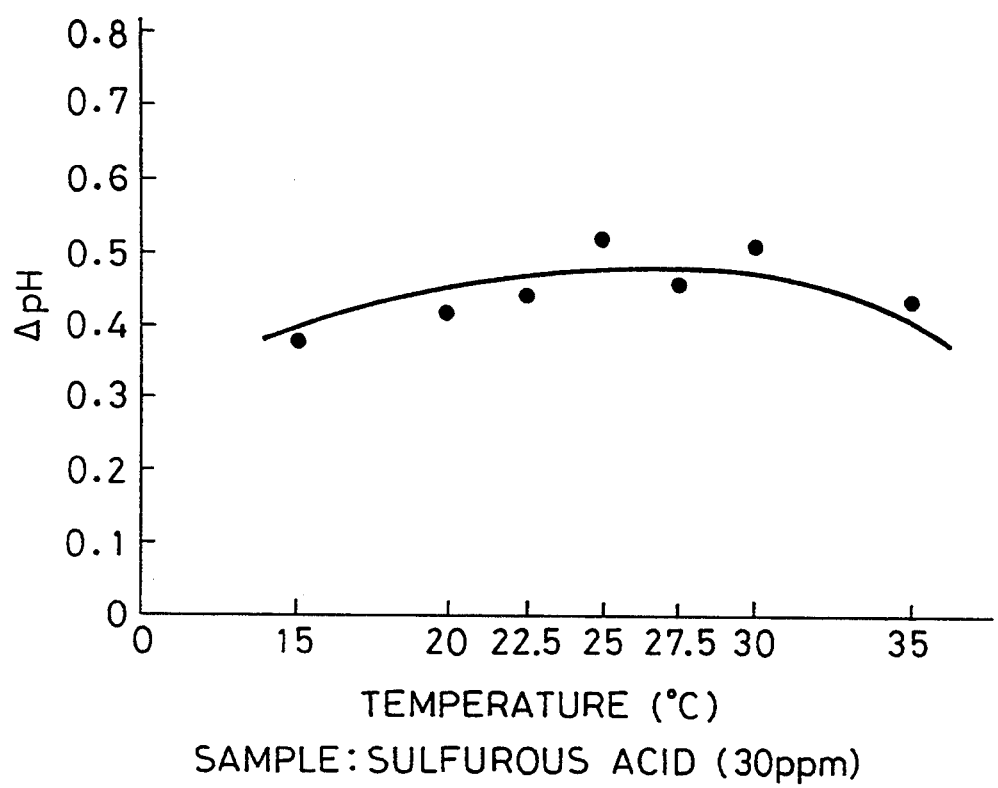
FIG. 11 is a graph representing the relationship between the pH change and the temperature for measurement.

The suitable temperature range for measuring the sulfurous acid content by monitoring the change in pH was found to be 15°–30° C. Within this range, the temperature for measurement had almost no influence on the change in the pH (see FIG. 11). FIG. 11 shows the relationship between the change in the pH and the temperature for measurement under conditions; 10 minutes for measurement, starting pH 5.0, and 2.5 mM sodium phosphate buffer solution containing 0.1M NaCl.

5) Amount of Bacterial Cells for Measurement

Figure 12:
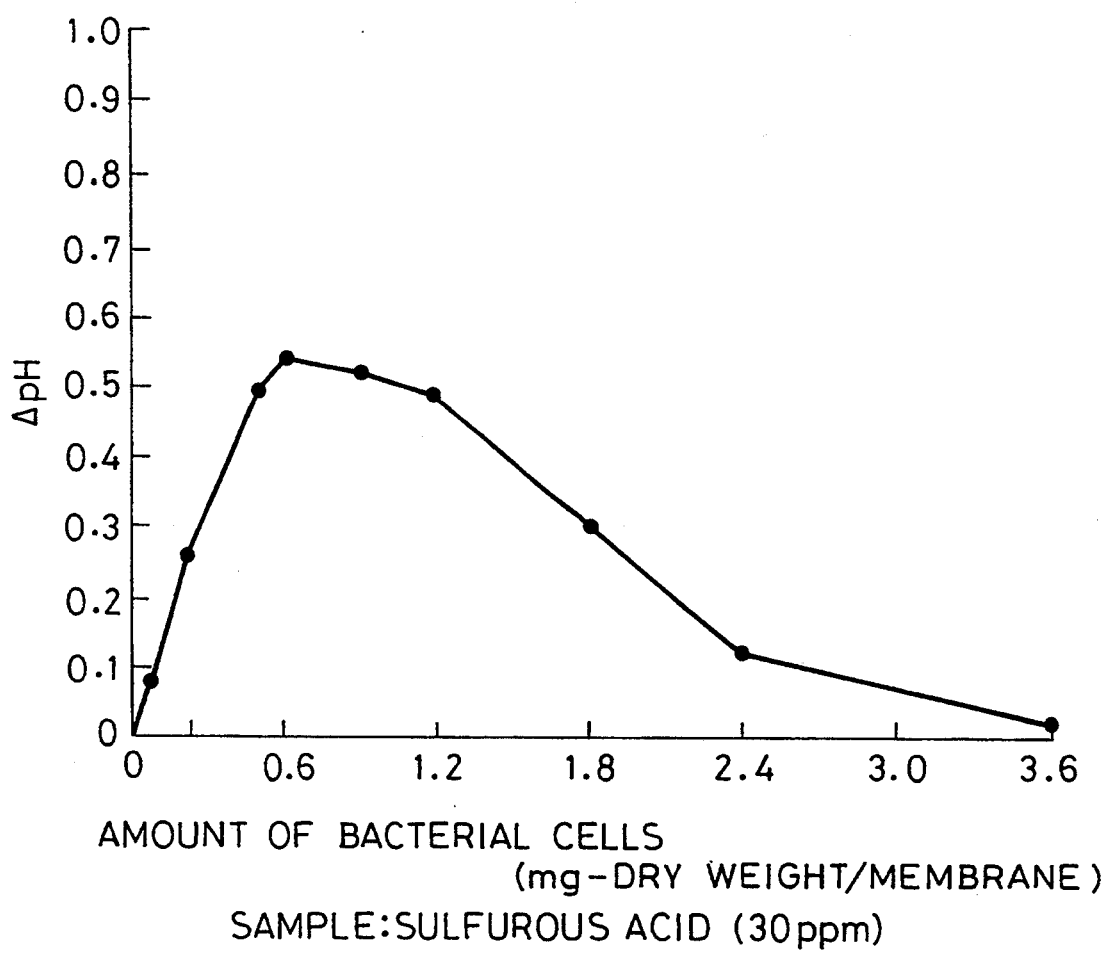
FIG. 12 is a graph representing the relationship between the pH change and the amount of immobilized bacterial cells used.

Various amounts of bacterial cells were immobilized on membranes as described in Example 3 and pH change was measured using the membranes. A suitable amount of bacterial cells was 0.5–1.8 mg-dry weight-/membrane (see FIG. 12). FIG. 12 shows the relationship between pH change and an amount of bacterial cells under conditions; 10 minutes for measurement, starting pH 5.0, 30° C. and 2.5 mM sodium phosphate buffer solution containing 0.1M NaCl.

Figure 13:
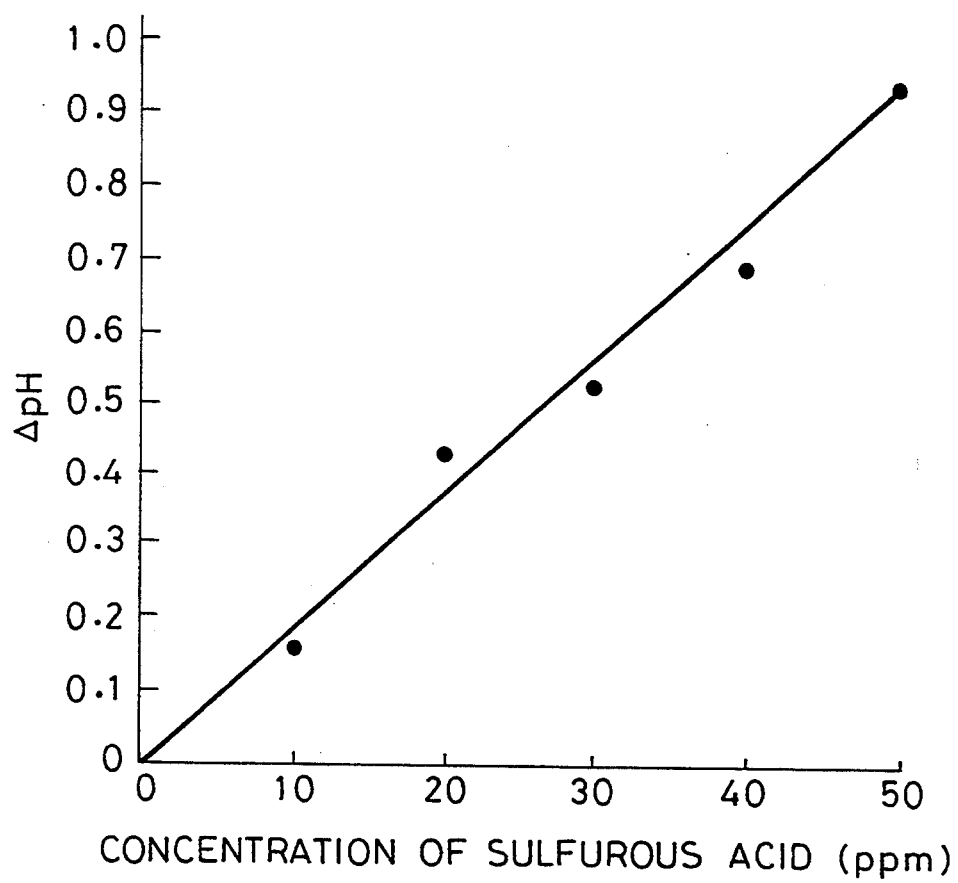
FIG. 13 is a graph representing the calibration curve of sulfurous acid concentration.

6) Calibration Curve of Sulfurous Acid 0.6 mg of bacterial cells (dry weight) were immobilized on a membrane and the bacterial-cell-immobilized membrane was plugged into the glass electrode of a pH meter (biosensor equipped pH meter). Samples were measured in 2.5 mM sodium phosphate buffer solution/pH 5.0. Samples containing 0-50 ppm of sulfurous acid were measured at 30° C. for 10 minutes in a sample chamber equipped with biosensor equipped pH meter. The linear curve in FIG. 13 illustrates the relationship between concentration of sulfurous acid in a sample and pH change under conditions 10 minutes for measurement, starting pH 5.0, 30° C., 0.6 mg of bacterial cells and 2.5 mM sodium phosphate buffer solution containing 0.1M NaCl. The linear relationship demonstrates that the concentration of sulfurous acid in a sample can be measured by the biosensor equipped pH meter.

The sulfurous acid content in white wine was then measured using the biosensor equipped pH meter. The data obtained was comparable to the data obtained by Rankine's method.

Compared to the microbe-electrode of the invention, the biosensor equipped pH meter has the following advantages: 1) dissolved oxygen in a sample does not affect measurement, 2) temperature change has minimum effects on measured values, 3) equipment is inexpensive, 4) smaller sizes of the equipment is available.

EXAMPLE 3

(2) Culture Method of *Thiobacillus thiooxidans*

*Thiobacillus thiooxidans* 20294 (FERM BP-3467) was inoculated into 50 ml of a medium (described below) in a 200 ml Erlenmeyer flask.

| Medium composition | |
|---|---|
| Powdered sulfur | 1.0% |
| $K_2HPO_4$ | 0.05 |
| $Ca(NO_3)_2 4H_2O$ | 0.001% |
| $(NH_4)_2SO_4$ | 0.3% |
| KCl | 0.01% |
| $MgSO_4 7H_2O$ | 0.05% |

**The chemical agent was dissolved in distilled water and the pH was adjusted to pH 6.5

The culture was incubated with shaking at 30° C. for 4 days. After incubation, 2 ml of the 4-day culture was added to 100 ml of the same medium as described above in a 300 ml Erlenmeyer flask. The mixture was incubated with shaking at 30° C. for 10 days. After incubation, the culture was filtrated using No. 5C filter (Toyo Roshi) to remove sulfur. The resulting filtrate was found to contain 0.4 g/l (dry weight) of bacterial cells.

(2) Culture of Bacteria Belonging to *Thiobacillus thiooxidans* and *Thiobacillus ferrooxidans* and Comparison of Oxygen Uptake Rate.

The bacteria belonging to *Thiobacillus thiooxidans* or *Thiobacillus ferrooxidans* (see Table 1) were inoculated into 100 ml of the medium described in (1) in a 300 ml Erlenmeyer flask to a final concentration of 1 mg/l of bacterial cells (dry weight). The culture was incubated with shaking at 30° C. for 4 days. After incubation, the culture was filtrated using No. 5C filter (Toyo Roshi) to remove sulfur. The bacterial cell thus obtained was weighed to measure its growth rate and tested for an oxygen uptake rate as an indicator for ability of oxidizing sulfurous acid.

The oxygen consumption is measured by an oxygen uptake meter (Rank Broth. Co.) using an increased concentration of sodium sulfite standard. Table 1 shows the results.

EXAMPLE 4

The bacteria listed in Table 9 was inoculated into 100 ml of the medium described in (1) in a 300ml Erlenmeyer flask to a final concentration of 10 mg/l of bacterial cells (dry weight). The culture was incubated with shaking at 30° C. for 4 days. After incubation, the culture was filtrated using No. 5C filter (Toyo Roshi) to remove sulfur. The filtrate described in (2) was centrifuged at 11,000 rpm for 15 minutes. The cell pellet was suspended in a small amount of ice cold distilled water and then the suspension was centrifuged for washing the cells. The washing procedure was repeated twice.

After washing, the cell was resuspended in 0.1M sodium citrate-NaOH buffer solution/pH 6.0 to a final concentration of 5 g/l (dry weight). The suspension was incubated in a thermostat at 30° C. for a week. After incubation, the bacterial cell was tested for its oxygen consumption using a sodium sulfite standard as described in Example 2. Table 9 shows the results.

TABLE 9

| Bacterial strain | Oxygen uptake rate (mgO2/minute/g-dry weight) |
|---|---|
| *Thiobacillus thiooxidans* | |
| IFO 13724 | 1 |
| JCM 3866 | 2 |
| JCM 3867 | 1 |
| JCM 3868 | 2 |
| 11773 | 4 |
| 20294 | 11 |

*Thiobacillus thiooxidans* 20294 of the invention was found to maintain a strong enzymatic activity even after one week incubation at 30° C.

What is claimed is:

1. A method for measuring a total sulfurous acid content of a sample comprising the steps of:
   a) converting any bound sulfurous acid present in the sample to free sulfurous acid by adjusting the pH of the sample within the range of from about 1 to 3, and holding the sample at a temperature of between 70° and 110° C. for between 2 and 25 minutes;
   b) oxidizing any free sulfurous acid in the sample to sulfuric acid using *Thiobacillus thiooxidans* 20294 (FERN BP-3467); and
   c) measuring the amount of free sulfurous acid oxidized in the sample.

2. The method of claim 1 wherein the pH of the sample is adjusted to between 1.5 and 3.0.

3. The method of claim 1 wherein the sample is held at between 75° and 105° C.

4. The method of claim 2 wherein the sample is held at between 75° and 105° C.

5. A method for measuring a total sulfurous acid content of a sample comprising the steps of:
   a) converting any bound sulfurous acid present in the sample to free sulfurous acid by adjusting the pH of the sample within the range from about 10-14, and holding the sample at a temperature of between 15° and 70° C. for between 2 and 20 minutes;
   b) oxidizing any free sulfurous acid in the sample to sulfuric acid using *Thiobacillus thiooxidans* 20294 (FERM BP-3467); and
   c) measuring the amount of free sulfurous acid oxidized in the sample.

6. The method of claim 5 wherein the pH of the sample is adjusted to between 11 and 13.

7. The method of claim 5 wherein the sample is held at between 20° and 50° C.

8. The method of claim 6 wherein the sample is held at between 20° and 50° C.

9. A method for measuring a bound sulfurous acid content in a sample comprising the steps of:
   a) measuring any free sulfurous acid content in the sample by oxidizing any free sulfurous acid in the sample to sulfuric acid using *Thiobacillus thiooxidans* 20294 (FERM BP-3467), and measuring the amount of free sulfurous acid oxidized in the sample;
   b) measuring a total sulfurous acid content in the sample by converting any bound sulfurous acid in the sample to free sulfurous acid by adjusting the pH of the sample within the range from about 1 to 3, holding the sample at a temperature of between 70° and 110° C. for between 2 and 25 minutes, oxidizing any free sulfurous acid in the sample to sulfuric acid using *Thiobacillus thiooxidans* 20294 (FERM BP-3462), and measuring the amount of free sulfurous acid oxidized in the sample; and
   c) subtracting the value of the free sulfurous acid content in the sample from the value of the total sulfurous acid content in the sample to obtain the value of the bound sulfurous acid content in the sample.

10. A method for measuring a bound sulfurous acid content in a sample comprising the steps of:
    a) measuring any free sulfurous acid content in the sample by oxidizing any free sulfurous acid in the sample to sulfuric acid using *Thiobacillus thiooxidans* 20294 (FERM BP-3467), and measuring the amount of free sulfurous acid oxidized in the sample;
    b) measuring a total sulfurous acid content in the sample by converting any bound sulfurous acid in the sample to free sulfurous acid by adjusting the pH of the sample within the range from about 10 to 14, holding the sample at a temperature of between 15° and 70° C. for between 2 and 20 minutes, oxidizing any free sulfurous acid in the sample to sulfuric acid using *Thiobacillus thiooxidans* 20294 (FERM BP-3467), and measuring the amount of free sulfurous acid oxidized in the sample; and
    c) subtracting the value of the free sulfurous acid content in the sample from the value of the total sulfurous acid content in the sample to obtain the value of the bound sulfurous acid content in the sample.

11. A method for measuring an amount of free sulfurous acid oxidized to sulfuric acid in a sample comprising the steps of:
    a) diluting the sample in a buffer, the buffer having a pH of from about 4.5 to 6.0;
    b) oxidizing any free sulfurous acid in the diluted sample to sulfuric acid using *Thiobacillus thiooxidans* 20294 (FERM BP-3467); and
    c) determining the amount of free sulfurous acid oxidized to sulfuric acid by measuring any change in pH of the diluted sample, wherein the pH change is proportional to the amount of free sulfurous acid oxidized to sulfuric acid in the sample.

12. The method of claim 11 wherein the buffer comprises 2.5 mM sodium phosphate and 0.1M NaCl.

13. The method of claim 11 wherein the sample and buffer solution are maintained at a temperature of from about 15° to 35° C.

14. The method of claim 12 wherein the sample and buffer solution are maintained at a temperature of from about 15° to 35° C.

15. The method of claim 11 wherein the oxidation step is performed by 0.5–1.8 mg-dry weight of bacteria per volume of liquid.

* * * * *